(12) United States Patent
Keidar (10) Patent No.: US 6,650,927 B1
(45) Date of Patent: Nov. 18, 2003

(54) RENDERING OF DIAGNOSTIC IMAGING DATA ON A THREE-DIMENSIONAL MAP

(75) Inventor: Yaron Keidar, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 349 days.

(21) Appl. No.: 09/643,666

(22) Filed: Aug. 18, 2000

(51) Int. Cl.[7] ................................................ A61B 5/00
(52) U.S. Cl. ...................................................... 600/424
(58) Field of Search ................................ 600/407, 424, 600/374, 508, 468; 128/899; 607/122

(56) References Cited

U.S. PATENT DOCUMENTS

| | | | |
|---|---|---|---|
| 3,316,896 A | 5/1967 | Thomasset | |
| 4,157,572 A | 6/1979 | Kennedy et al. | 360/33 |
| 4,459,990 A | 7/1984 | Barnea | 128/656 |
| 4,522,212 A | 6/1985 | Gelinas et al. | 128/642 |
| 4,628,937 A | 12/1986 | Hess et al. | 128/642 |
| 4,630,203 A | 12/1986 | Szirtes | 364/414 |
| 4,660,571 A | 4/1987 | Hess et al. | 128/784 |
| 4,682,603 A | 7/1987 | Franz | 128/642 |
| 4,699,147 A | 10/1987 | Chilson et al. | 128/642 |
| 4,762,124 A | 8/1988 | Kerch et al. | 128/156 |
| 4,875,165 A | 10/1989 | Fencil et al. | 364/413.22 |
| 4,878,115 A | 10/1989 | Elion | 358/111 |
| 4,898,181 A | 2/1990 | Kessier | 128/699 |
| 4,905,705 A | 3/1990 | Kizakevich et al. | 128/696 |
| 4,911,174 A | 3/1990 | Pederson et al. | 128/695 |
| 4,922,912 A | 5/1990 | Watanabe | 128/642 |

(List continued on next page.)

FOREIGN PATENT DOCUMENTS

| | | |
|---|---|---|
| EP | 0 501 993 B1 | 6/1997 |
| EP | 0 974 936 A2 | 1/2000 |
| WO | WO 94/04938 | 3/1994 |
| WO | WO 94/06349 | 3/1994 |
| WO | WO 96/05768 | 2/1996 |
| WO | WO 97/24983 | 6/1997 |
| WO | WO 97/24981 A2 | 7/1997 |
| WO | WO 97/24981 A3 | 7/1997 |
| WO | WO 97/25101 | 7/1997 |
| WO | WO 98/12663 | 3/1998 |
| WO | WO 98/35720 A3 | 8/1998 |
| WO | WO 98/35720 A2 | 8/1998 |
| WO | WO 99/05971 | 2/1999 |
| WO | WO 00/07501 | 2/2000 |

OTHER PUBLICATIONS

Gerstenfeld E., Sahakian A., Swiryn S.; Evidence for Transient Linking of Atrial Excitation During Atrial Fibrillation in Humans (1992); Circulation vol. 86, No. 2, pp 375–382.

(List continued on next page.)

Primary Examiner—Shawna J. Shaw
(74) Attorney, Agent, or Firm—Louis J. Capezzuto (57) ABSTRACT

A method and apparatus for mapping a structure in a body of a subject includes capturing a three-dimensional (3D) image of the structure comprising diagnostic information, and generating a 3D geometrical map of the structure using a probe inserted into the structure. The image is registered with the map, such that each of a plurality of image points in the image is identified with a corresponding map point in the map. The map is displayed such that the diagnostic information associated with each of the image points is displayed at the corresponding map point.

40 Claims, 7 Drawing Sheets

U.S. PATENT DOCUMENTS

| | | | |
|---|---|---|---|
| 4,940,064 A | 7/1990 | Desai | 128/784 |
| 4,955,382 A | 9/1990 | Franz et al. | 128/642 |
| 4,962,767 A | 10/1990 | Brownlee | 128/786 |
| 4,979,510 A | 12/1990 | Franz et al. | 128/642 |
| 5,022,396 A | 6/1991 | Watanabe | 128/642 |
| 5,038,791 A | 8/1991 | Collins et al. | 128/696 |
| 5,042,486 A | 8/1991 | Pfeiler et al. | 128/653 |
| 5,056,524 A | 10/1991 | Oe | 128/654 |
| 5,127,403 A | 7/1992 | Brownlee | 128/419 P |
| 5,156,151 A | 10/1992 | Imran | 128/642 |
| 5,175,773 A | 12/1992 | Garreau et al. | 382/6 |
| 5,215,103 A | 6/1993 | Desai | 128/784 |
| 5,227,969 A | 7/1993 | Waggener et al. | 364/413.26 |
| 5,228,442 A | 7/1993 | Imran | 128/642 |
| 5,231,995 A | 8/1993 | Desai | 128/784 |
| 5,239,999 A | 8/1993 | Imran | 128/642 |
| 5,243,981 A | 9/1993 | Hudrlik | 607/11 |
| 5,255,678 A | 10/1993 | Deslauriers et al. | 128/642 |
| 5,255,679 A | 10/1993 | Imran | 128/642 |
| 5,279,299 A | 1/1994 | Imran | 128/642 |
| 5,293,869 A | 3/1994 | Edwards et al. | 128/642 |
| 5,297,549 A | 3/1994 | Beatty et al. | 128/642 |
| 5,311,866 A | 5/1994 | Kagan et al. | 128/642 |
| 5,313,943 A | 5/1994 | Houser et al. | 128/642 |
| 5,324,284 A | 6/1994 | Imran | 606/15 |
| 5,341,807 A | 8/1994 | Nardella | 128/642 |
| 5,345,936 A | 9/1994 | Pomeranz et al. | 138/642 |
| 5,383,917 A | 1/1995 | Desai et al. | 607/102 |
| 5,391,199 A | 2/1995 | Ben-Haim | 607/122 |
| 5,409,000 A | 4/1995 | Imran | 128/642 |
| 5,433,198 A | 7/1995 | Desai | 128/642 |
| 5,443,489 A | 8/1995 | Ben-Haim | 607/115 |
| 5,454,370 A | 10/1995 | Avitall | 128/642 |
| 5,471,982 A | 12/1995 | Edwards et al. | 128/642 |
| 5,485,849 A | 1/1996 | Panescu et al. | 128/699 |
| 5,487,391 A | 1/1996 | Panescu | 128/699 |
| 5,515,853 A | 5/1996 | Smith et al. | 128/661.01 |
| 5,531,227 A | 7/1996 | Schneider | 128/653.1 |
| 5,546,951 A | 8/1996 | Ben-Haim | 128/702 |
| 5,549,109 A | 8/1996 | Samson et al. | 128/642 |
| 5,588,432 A | 12/1996 | Crowley | 128/660.03 |
| 5,595,183 A | 1/1997 | Swanson et al. | 128/697 |
| 5,637,090 A | 6/1997 | McGee et al. | 604/95 |
| 5,657,755 A | 8/1997 | Desai | 128/642 |
| 5,687,737 A * | 11/1997 | Branham et al. | |
| 5,697,377 A | 12/1997 | Wittkampf | 128/696 |
| 5,718,241 A | 2/1998 | Ben-Haim et al. | 128/702 |
| 5,730,704 A | 3/1998 | Avitall | 600/374 |
| 5,738,096 A | 4/1998 | Ben-Haim | 128/653.1 |
| 5,755,664 A | 5/1998 | Rubenstein | 600/377 |
| 5,840,031 A | 11/1998 | Crowley | 600/440 |
| 5,842,984 A | 12/1998 | Avitall | 600/374 |
| 5,889,524 A | 3/1999 | Sheehan et al. | 345/419 |
| 5,921,924 A | 7/1999 | Avitall | 600/374 |
| 5,931,835 A | 8/1999 | Mackey | 606/34 |
| 5,931,863 A | 8/1999 | Griffin, III et al. | 607/122 |
| 5,999,587 A | 12/1999 | Ning et al. | 378/4 |
| 6,052,618 A | 4/2000 | Dahlke et al. | 600/523 |
| 6,066,094 A | 5/2000 | Ben-Haim | 600/437 |
| 6,226,542 B1 * | 5/2001 | Reisfeld | 600/407 |
| 6,295,464 B1 * | 9/2001 | Metaxas | 600/407 |
| 6,389,310 B1 * | 5/2002 | Demonceau et al. | 600/512 |

OTHER PUBLICATIONS

Gerstenfeld E., Sahakian A., Baerman J., Ropella K., Swiryn S.; Detection of Changes in Atrial Endocardial Activation With Use of an Orthogonal Catheter (1991); JACC vol. 18, No. 4, pp 1034–1042.

Kadish A., Spear J., Levine J., Hanich R., Prood C., Moore E.; Vector Mapping of Myocardial Activation (1986); Laboratory Investigation Arrhythmia vol. 74, No. 3, pp 603–615.

Terzopoulos D.; Transactions on Pattern Analysis and Machine Intelligence (1986), vol. PAMI–8, No. 4; Regularization of Inverse Visual Problems Involving Discontinuities; pp 413–424.

Lai et al.; IEEE Transactions on Pattern Analysis and Machine Intelligence (1995) vol. 17, No. 11; Deformable Contours: Modeling and Extraction; pp 1084–1090.

Onnasch et al.; Computers in Cardiology, Long Beach, CA, IEEE Computer Society (1975); A Versatile Program for the Documentation and Comparison of Traced Heart Contours; pp 257–262.

Duda et al.; Communications of the ACM (1972) vol. 15, No. 1; Use of the Hough Transormation to Detect Lines and Curves in Pictures; pp 11–15.

Kass et al.; Proceedings of First International Conference Vision (1987); Snakes: Active Contour Models; pp 259–268.

Jain, A.K.; Fundamentals of Digital Image Processing (1989); "The Back–Projection Operator"; pp. 445.

Foley J.D., van Dam A., Feiner S.K., Hughes J.F.; 2nd Edition in C Computer Graphics Principles and Practice (1986);"Filling Algorithms"; pp. 979–986.

Castleman, K.R.; Digital Image Processing (1996); "Curve and Surface Fitting"; pp. 501–507.

Besl, Paul J., *Member, IEEE*, and McKay, Neil D.; IEEE Transactions on Pattern Analysis and Machine Intelligence, vol. 14, No. 2, Feb. 1992; A Method for Registration of 3–D Shapes; pp. 239–256.

Fang, Shu–Cherng; Puthenpura, Sarat; AT&T; Linear Optimization and Extensions: Theory and Algorithms; Complexity Analysis and the Ellipsoid Method, Chap. 5, pp. 96–103.

Lai, Kok Fung; Thesis, University of Wisconsin–Madison 1994; Deformable Contours; Modeling, Extraction, Detection and Classification; 96 pgs.

Umeyama, Shinji; IEEE Transactions on Pattern Analysis and Machine Intelligence, vol. 13, No. 4, Apr. 1991; Least–Squares Estimation of Transformation Parameters Between Two Point Patterns; pp. 376–380.

Freeman, H.; "Computer Processing of Line Drawing Images"; Computing Surveys 6, 1974, pp. 57–97.

* cited by examiner

RENDERING OF DIAGNOSTIC IMAGING DATA ON A THREE-DIMENSIONAL MAP

FIELD OF THE INVENTION

The present invention relates generally to systems and methods for three-dimensional mapping and reconstruction, and specifically to mapping and reconstruction of the interior of body organs, such as the heart.

BACKGROUND OF THE INVENTION

Various methods of diagnostic imaging are known in the art. Methods used for imaging the heart, for example, include fluoroscopy, angiography, echocardiography, computed tomography (CT), magnetic resonance imaging (MRI), positron emission tomography (PET) and single photon emission tomography (SPECT). Many of these methods produce three-dimensional (3D) image information, which can then be rendered for viewing in the form of parallel slices through the heart, or as a pseudo-3D display on a video monitor. In order to administer treatment, the treating physician must build a 3D picture in his or her mind based on the two-dimensional pictures that are displayed. The transposition is particularly tricky when therapy is to be administered inside the heart, such as local electrical ablation of aberrant electrical pathways, or laser myocardial revascularization.

It is also known in the art to map the heart using a mapping probe, typically a catheter, inside the heart chambers. Exemplary methods and devices for this purpose are described in U.S. Pat. Nos. 5,471,982 and 5,391,199 and in PCT patent publications WO94/06349, WO96/05768 and WO97/24981, whose disclosures are incorporated herein by reference. U.S. Pat. No. 5,391,199, for example, describes a catheter that includes both electrodes for sensing cardiac electrical activity and miniature coils for determining the position of the catheter relative to an externally-applied magnetic field. Using this catheter a cardiologist can collect data from a set of sampled points in the heart within a short period of time, by measuring the electrical activity at a plurality of locations and determining the spatial coordinates of the locations. Locations of the mapping catheter within the heart can be superimposed on a 3D reconstruction of an image of the heart, such as an ultrasound image, acquired prior to or during the catheter study. Color codes are used to represent electrical activity sensed by the catheter.

U.S. Pat. No. 5,738,096, whose disclosure is incorporated herein by reference, describes methods for geometrical mapping of the endocardium based on bringing a probe into contact with multiple locations on a wall of the heart, and determining position coordinates of the probe at each of the locations. The position coordinates are combined to form a map of at least a portion of the heart. Once the position of the catheter is known, external sensors can be used to provide local physiological values of heart tissue adjacent to the tip of the catheter. For example, if the catheter incorporates a radioactive marker suitable for SPECT, local functional information can be gleaned from a SPECT image. Yet another example is determining local perfusion from Doppler-ultrasound images of the coronaries, from nuclear medicine images or from X-ray or CT angiography, and overlaying the perfusion map on the geometrical map. The image of the catheter in the perfusion map can be used to align the perfusion map and the geometrical map. Alternatively, the alignment may be carried out using fiducial marks or anatomical reference locations, either automatically or manually.

Further methods for creating a three-dimensional map of the heart based on these data are disclosed, for example, in European patent application EP 0 974 936 and in a corresponding U.S. patent application Ser. No. 09/122,137 now U.S. Pat. No. 6,226,542 issued May 1, 2001, which is assigned to the assignee of the present patent application, and whose disclosure is incorporated herein by reference. As indicated in these applications, position coordinates (and optionally electrical activity, as well) are initially measured at about 10 to 20 points on the interior surface of the heart. These data points are generally sufficient to generate a preliminary reconstruction or map of the cardiac surface to a satisfactory quality. The preliminary map is preferably combined with data taken at additional points in order to generate a more comprehensive map.

SUMMARY OF THE INVENTION

It is an object of some aspects of the present invention to provide improved methods and apparatus for mapping and visualization of internal body structures, and particularly of the heart.

It is a further object of some aspects of the present invention to provide improved methods and apparatus for administering local treatment of pathological conditions within the heart.

In preferred embodiments of the present invention, a position-sensing catheter is used to generate a 3D geometrical map of the internal surface of a heart chamber of a subject. A 3D diagnostic image of the heart is captured in conjunction with generating the 3D map, typically either before or concurrently with the mapping. The image and map are brought into mutual registration, and diagnostic information from the image, such as perfusion information, is then marked on the 3D map, preferably in the form of color coding. Based on the combined diagnostic and geometrical information, a physician operating the catheter is able to identify and visualize areas of the heart that are in need of treatment, due to low perfusion, for example. The physician preferably uses the catheter to apply a local invasive therapy, such as laser revascularization, to specific points that are located using the color-coded 3D map. Alternatively, a local diagnostic technique, such as a biopsy, may be performed at such specific points.

There is therefore provided, in accordance with a preferred embodiment of the present invention, a method for mapping a structure in a body of a subject, including:

capturing a three-dimensional (3D) image of the structure including diagnostic information;

generating a 3D geometrical map of the structure using a probe inserted into the structure;

registering the image with the map, such that each of a plurality of image points in the image is identified with a corresponding map point in the map; and displaying the map, such that the diagnostic information associated with each of the image points is displayed at the corresponding map point.

In a preferred embodiment, the diagnostic information is related to blood flow in the structure, wherein the diagnostic information includes local perfusion data. In other preferred embodiments, the diagnostic information includes metabolic data, or is related to uptake of a substance in tissue of the structure, or is related to motion of the structure.

Preferably, generating the geometrical map includes bringing the probe into contact with the structure at a multiplicity of locations on the structure, and recording position coordinates of the probe at the locations, wherein recording the position coordinates includes determining the coordinates using a position sensor in the probe.

Preferably, registering the image with the map includes applying a transformation to at least one of the image and the map so that following the transformation, the image and the map have a common axis and a common scale. Further preferably, registering the image with the map includes dividing the image into a plurality of parallel planar slices, perpendicular to the axis and mutually spaced along the axis, wherein the plurality of image points are located in the slices. More preferably, registering the image with the map includes finding an axial coordinate of each of the slices and an angular coordinate of each of the image points located in each of the slices, and identifying each of the image points with the map point having the same axial and angular coordinates. Most preferably, the structure includes a wall defining a cavity, and identifying each of the image points with the map point includes finding, at the axial and the angular coordinate, the image point that is within a section of the wall.

Preferably, displaying the map includes coloring the map to reflect the diagnostic information.

In a preferred embodiment, the method includes performing a medical procedure on the structure guided by the diagnostic information displayed on the map. Preferably, performing the medical procedure includes using the probe to perform the procedure locally at locations selected on the geometrical map, and the method includes marking on the geometrical map the locations at which the procedure was performed. Additionally or alternatively, performing the medical procedure includes performing a therapeutic procedure, wherein the diagnostic information relates to local blood flow in the structure, and wherein performing the therapeutic procedure includes performing a procedure for improving the local blood flow. Alternatively, performing the medical procedure includes performing a diagnostic procedure.

Preferably, the structure includes a heart of the subject, and generating the geometrical map includes mapping an endocardial surface in a ventricle of the heart.

There is also provided, in accordance with a preferred embodiment of the present invention, apparatus for mapping a structure in a body of a subject, including:

an imaging device, adapted to capture a three-dimensional (3D) image of the structure including diagnostic information;

a probe, adapted to be inserted into the structure, so as to generate a 3D geometrical map of the structure;

a processor, coupled to the probe and to the imaging device, and adapted to register the image with the map, such that each of a plurality of image points in the image is identified with a corresponding map point in the map; and a display, coupled to be driven by the processor to display the map, such that the diagnostic information associated with each of the image points is displayed at the corresponding map point.

The present invention will be more fully understood from the following detailed description of the preferred embodiments thereof, taken together with the drawings in which:

DETAILED DESCRIPTION OF PREFERRED EMBODIMENTS

Figure 1:
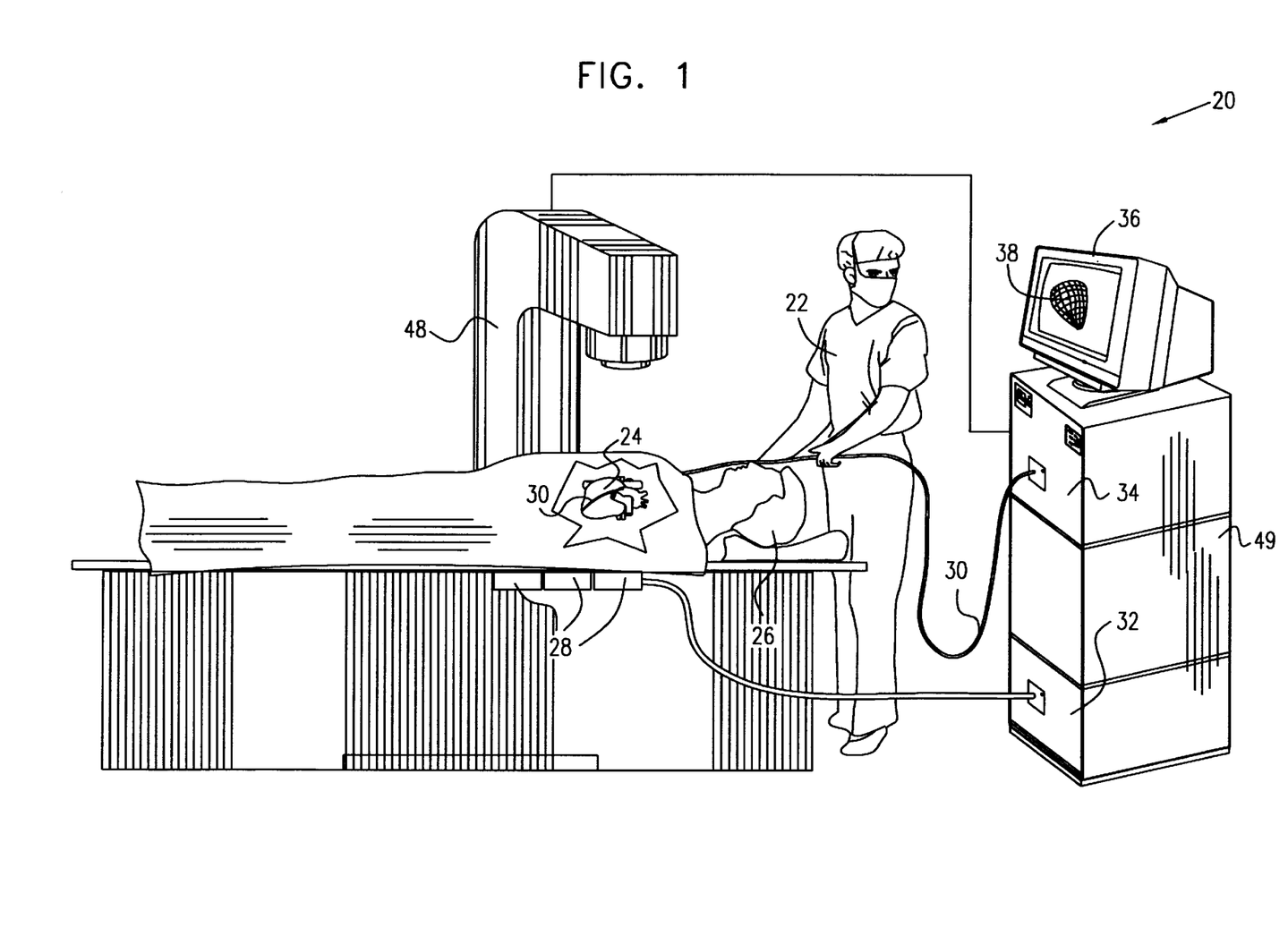
FIG. 1 is a schematic, pictorial illustration of a system for imaging, mapping and treatment of the heart, in accordance with a preferred embodiment of the present invention.

FIG. 1 is a schematic, pictorial illustration of a system 20 for three-dimensional geometrical mapping, imaging and treatment of a heart 24 of a subject 26, in accordance with a preferred embodiment of the present invention. System 20 comprises an elongate probe, preferably a catheter 30, which is inserted by a user 22 through a vein or artery of the subject into a chamber of the heart.

Catheter 30 preferably comprises at least one position sensor (not shown in the figures), most preferably located near the catheter's distal tip. The position sensor preferably comprises an electromagnetic sensor, which is mounted within the catheter by any suitable method, for example, using polyurethane glue or the like. The sensor is electrically connected to an electromagnetic sensor cable, which extends through the catheter body and into a control handle of the catheter. In the control handle, the wires of the sensor cable are connected to a circuit board (not shown), which amplifies the signals received from the electromagnetic sensor and transmits them to a computer housed in a console 34, in a form understandable to the computer. Because the catheter is designed for single use only, the circuit board preferably contains an EPROM chip, which shuts down the circuit board after the catheter has been used. This prevents the catheter, or at least the electromagnetic sensor, from being used twice.

To use the electromagnetic sensor, subject 26 is placed in a magnetic field generated, for example, by situating under the patient a pad containing field generator coils 28 for generating a magnetic field, driven by driver circuits 32. A reference electromagnetic sensor (not shown) is preferably fixed relative to the patient, e.g., taped to the patient's back, and catheter 30 containing its sensor is advanced into heart 24. The sensor preferably comprises three small coils, which in the magnetic field generate weak electrical signals indicative of their position in the magnetic field. Signals generated by both the fixed reference sensor and by the sensor in the heart are amplified and transmitted to console 34, which analyzes the signals and then displays the results on a monitor 36. By this method, the precise location of the sensor in the catheter relative to the reference sensor can be ascertained and visually displayed. The sensors can also detect displacement of the catheter that is caused by contraction of the heart muscle.

Suitable electromagnetic sensors for the purposes of the present invention are described, for example, in the above-mentioned U.S. Pat. No. 5,391,199 and PCT patent publication WO 96/05768. A preferred electromagnetic mapping sensor is manufactured by Biosense Ltd. (Tirat Hacarmel, Israel) and marketed under the trade designation NOGA. Some of the mapping features of catheter 30 and system 20 are implemented in the NOGA-STAR catheter marketed by Biosense Webster, Inc., and in the Biosense-NOGA system, also marketed by Biosense Webster, Inc. Further aspects of the design of catheter 30 and of system 20 generally are described in U.S. patent application Ser. No. 09/506,766, which is assigned to the assignee of the present patent application and is incorporated herein by reference. Using such sensors, system 20 achieves continuous generation of six dimensions of position and orientation information with respect to catheter 30. Alternatively, the sensors used in catheter 20 may comprise other types of position and/or coordinate sensors, as described, for example, in U.S. Pat. Nos. 5,391,199, 5,443,489 or 5,515,853, or in PCT publication WO 94/04938 or WO 99/05971, or substantially any other suitable type of position/coordinate sensing device known in the art.

As noted above, catheter 30 is coupled to console 34, which enables the user to observe and regulate the functions of the catheter. Console 34 includes a processor, preferably a computer with appropriate signal processing circuits (which are typically contained inside a housing of the computer). The processor is coupled to drive display 36. User 22 brings the distal tip of catheter 30 into contact with multiple points on the endocardial surface of heart 24, and the position coordinates are recorded at each point. The information derived from this analysis is used to reconstruct a three-dimensional geometrical map 38 of the endocardial surface of heart 24.

System 20 also comprises a diagnostic imaging unit 48, such as an echo Doppler unit, SPECT, PET, MRI, CT or other imaging unit known in the art. Unit 48 is used to capture a 3D diagnostic image of heart 24, preferably while user 22 is mapping the heart using catheter 30. Alternatively, the diagnostic image is captured before beginning the mapping, and unit 48 may, in this case, be separate from the other elements of system 20. Diagnostic data from the image captured by unit 48 are superimposed on map 38, using methods described hereinbelow. Depending on the type and configuration of unit 48, a wide range of different diagnostic data may be represented in the image, such as perfusion, metabolic factors, uptake of markers, heart wall motion or thickness, and/or other anatomical or electrical properties, as are known in the art. The image can also be timed to represent different phases in the heart cycle.

Typically, system 20 includes other elements, some of which are not shown in the figures for the sake of simplicity. In the present embodiment, the system preferably includes a laser console 49, which is used in performing direct myocardial revascularization, as described, for example, in PCT patent application PCT/IL97/00011 and in U.S. patent application Ser. No. 09/109,820, which is assigned to the assignee of the present patent application and whose disclosure is incorporated herein by reference. Console 49 injects laser energy into a suitable waveguide (not shown) within catheter 30. The waveguide conveys the energy to the distal tip of the catheter, where it is applied to revascularize areas of the myocardium suffering from low perfusion. Alternatively, the system may include other therapeutic elements, as are known in the art, particularly elements for delivering local treatment in the heart, such as a radio-frequency driver coupled to an ablation electrode on catheter 30; an ultrasound generator coupled to high-power transducer in the catheter, for ultrasonic ablation of the endocardium; or a supply of a therapeutic agent, such as growth factors for angiogenesis, coupled to an injection needle in the catheter. Still further alternatively, the system may include invasive diagnostic elements, such as biopsy forceps that are operated through catheter 30.

Other elements that may be comprised in system 20 are described, for example, in U.S. patent application Ser. No. 09/122,137, which is assigned to the assignee of the present patent application, and whose disclosure is incorporated herein by reference. Typically, system 20 includes an ECG monitor (not shown), coupled to receive signals from one or more body surface electrodes, so as to provide an ECG synchronization signal to console 34. As mentioned above, the system preferably also includes a reference position sensor, either on an externally-applied reference patch attached to the exterior of the patient's body, or on an internally-placed catheter, which is inserted into heart 24 and maintained in a fixed position relative to the heart. By comparing the position of catheter 30 to that of the reference catheter, the coordinates of catheter 30 are accurately determined relative to the heart, irrespective of heart motion. Alternatively, any other suitable method may be used to compensate for heart motion.

Figure 2:
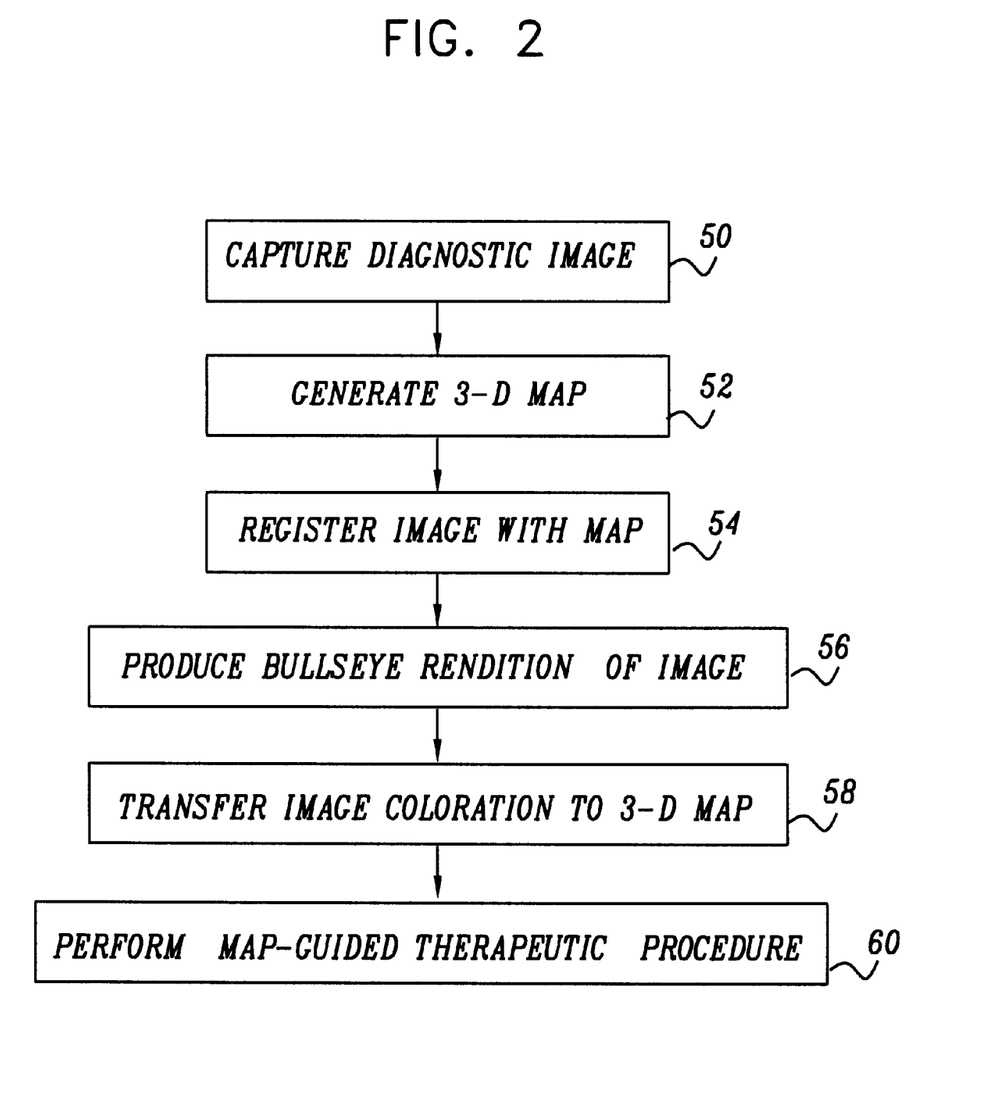
FIG. 2 is a flow chart that schematically illustrates a method for imaging, mapping and treating the heart, in accordance with a preferred embodiment of the present invention.

FIG. 2 is a flow chart that schematically illustrates a method for imaging, mapping and treatment of heart 24 using system 20, in accordance with a preferred embodiment of the present invention. At an imaging step 50, a diagnostic image of heart 24, such as a SPECT image, is captured. Preferably, although not necessarily, the image is captured while catheter 30 is already located inside the heart. The catheter is used to generate geometrical map 38, at a mapping step 52. Suitable mapping techniques for this purpose are described in the above-mentioned U.S. Pat. No. 5,738,096. The above-mentioned European patent application EP 0 974 936 and U.S. patent application Ser. No. 09/122,137 describe accurate methods for creating the map itself based on the data gathered using catheter 30. The image captured at step 50 and the map created at step 52 are then registered one with the other, at a registration step 54.

Figure 3:
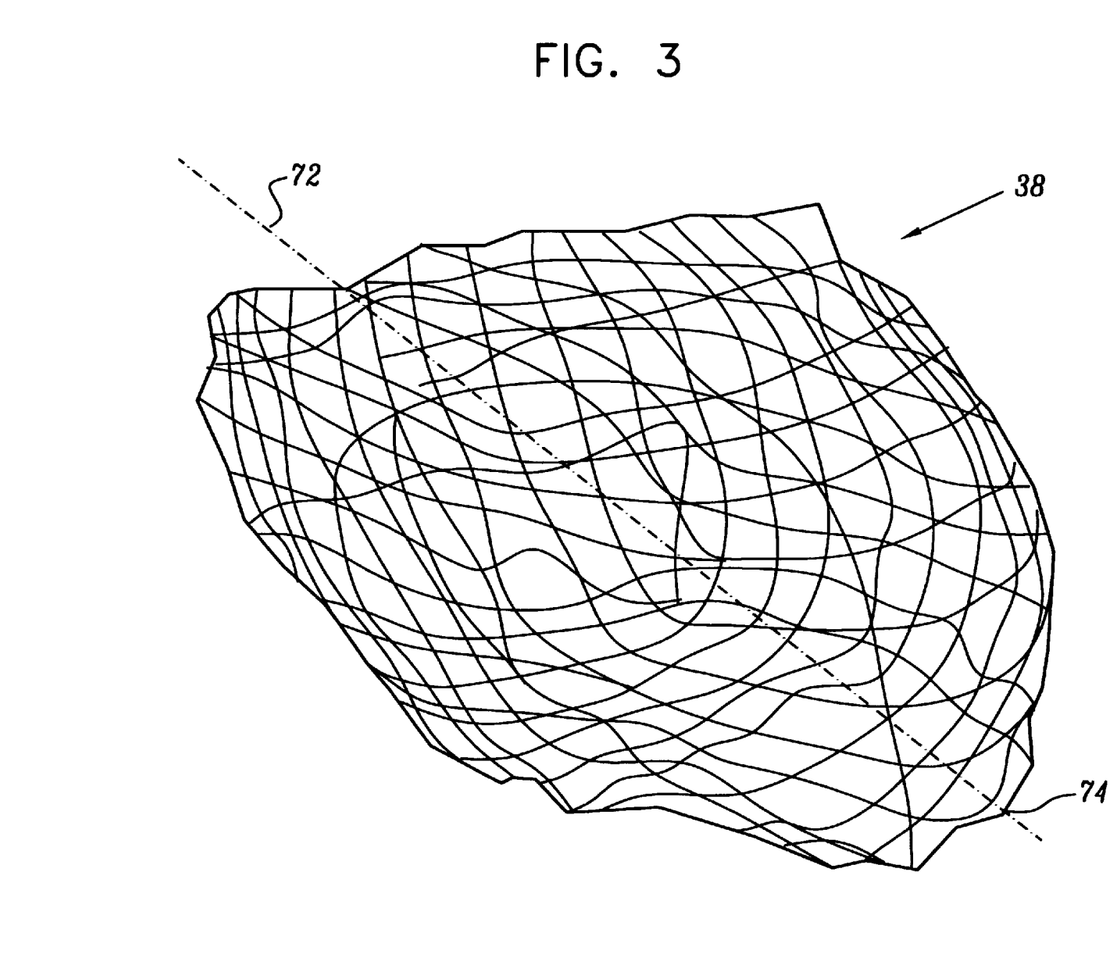
FIG. 3 is a schematic representation of a map of a chamber of the heart, in accordance with a preferred embodiment of the present invention.
Figure 4:
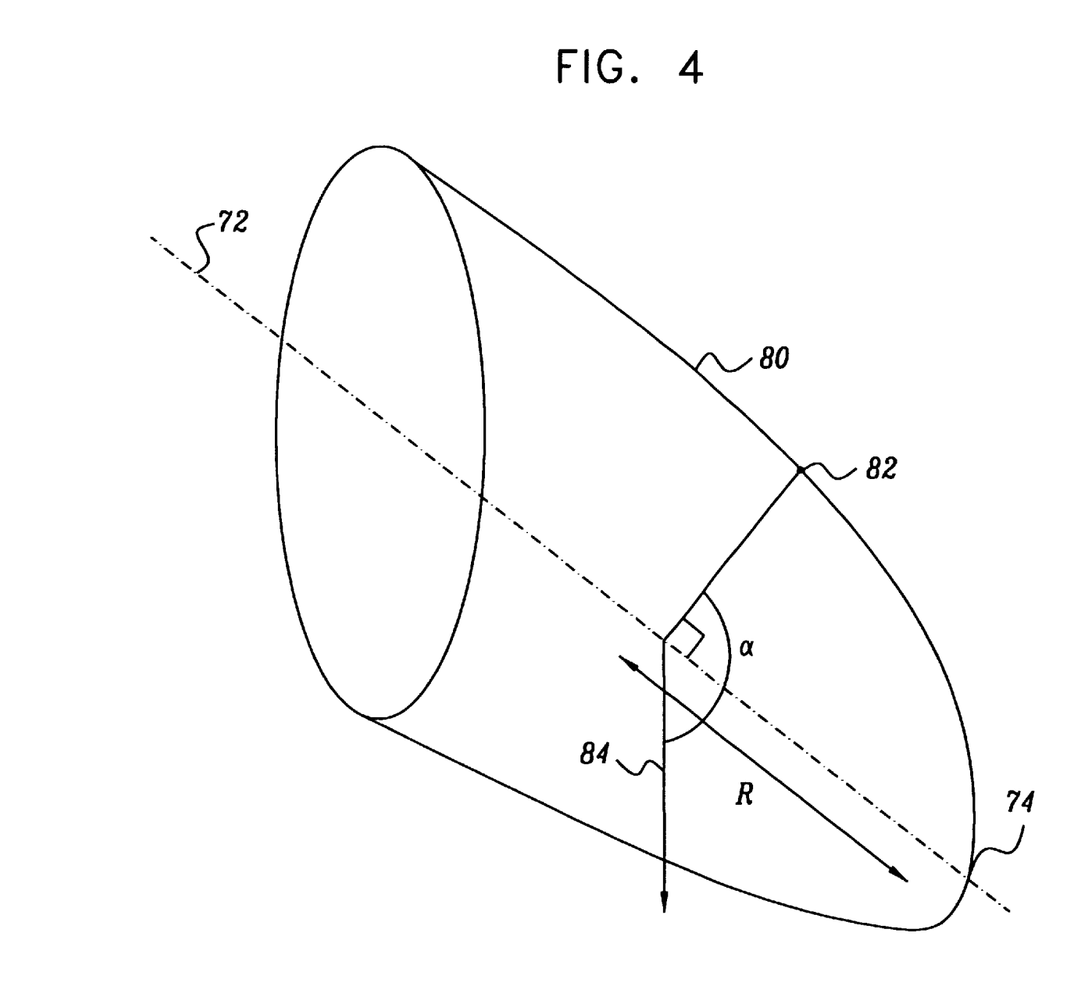
FIG. 4 is a simplified geometrical representation of the map of FIG. 3, showing coordinates used in registering the map with an image of the heart, in accordance with a preferred embodiment of the present invention.

FIGS. 3 and 4 are schematic representations of map 38 generated by system 20 at step 52, illustrating a method used at registration step 54, in accordance with a preferred embodiment of the present invention. FIG. 3 is a wire frame rendition of the map, representing the left ventricle of heart 24. For the purposes of step 54, a longitudinal axis 72 is drawn through the map, passing through an apex 74 of the ventricle. Preferably, the axis and apex are found automatically by console 34. Alternatively or additionally, these or other features of the map are identified manually by user 22.

FIG. 4 is a simplified geometrical representation of a surface 80 of map 38, generated for the purpose of registration with a diagnostic image of heart 24. Surface 80 corresponds to an approximate locus of the endocardium of the heart, as determined from map 38. A coordinate system is defined in which each point 82 on surface 80 is represented by a distance R from apex 74 and an angle a relative to a downward direction 84 (i.e., the direction pointing toward the feet of subject 26).

In order to register the diagnostic image with map 38, axis 72 and apex 74 are identified in the image, as well, and are aligned with the axis and apex of the map. The identification is preferably automatic but may, alternatively or additionally, be carried out or assisted by user 22. Other landmarks and/or fiducial marks in the heart can also be used in performing the alignment. The scale of the image is adjusted so that its dimensions match those of the map as closely as possible. For many types of diagnostic images, such as perfusion maps, the resolution of the diagnostic information is low, so that imprecision of as much as 10 mm in mutual registration can be tolerated. When higher resolution is required, the registration of the diagnostic image with the geometrical map may be improved using methods of automatic registration such as those described in Appendix A. These methods are optional and are not essential to the present invention.

Figure 5:
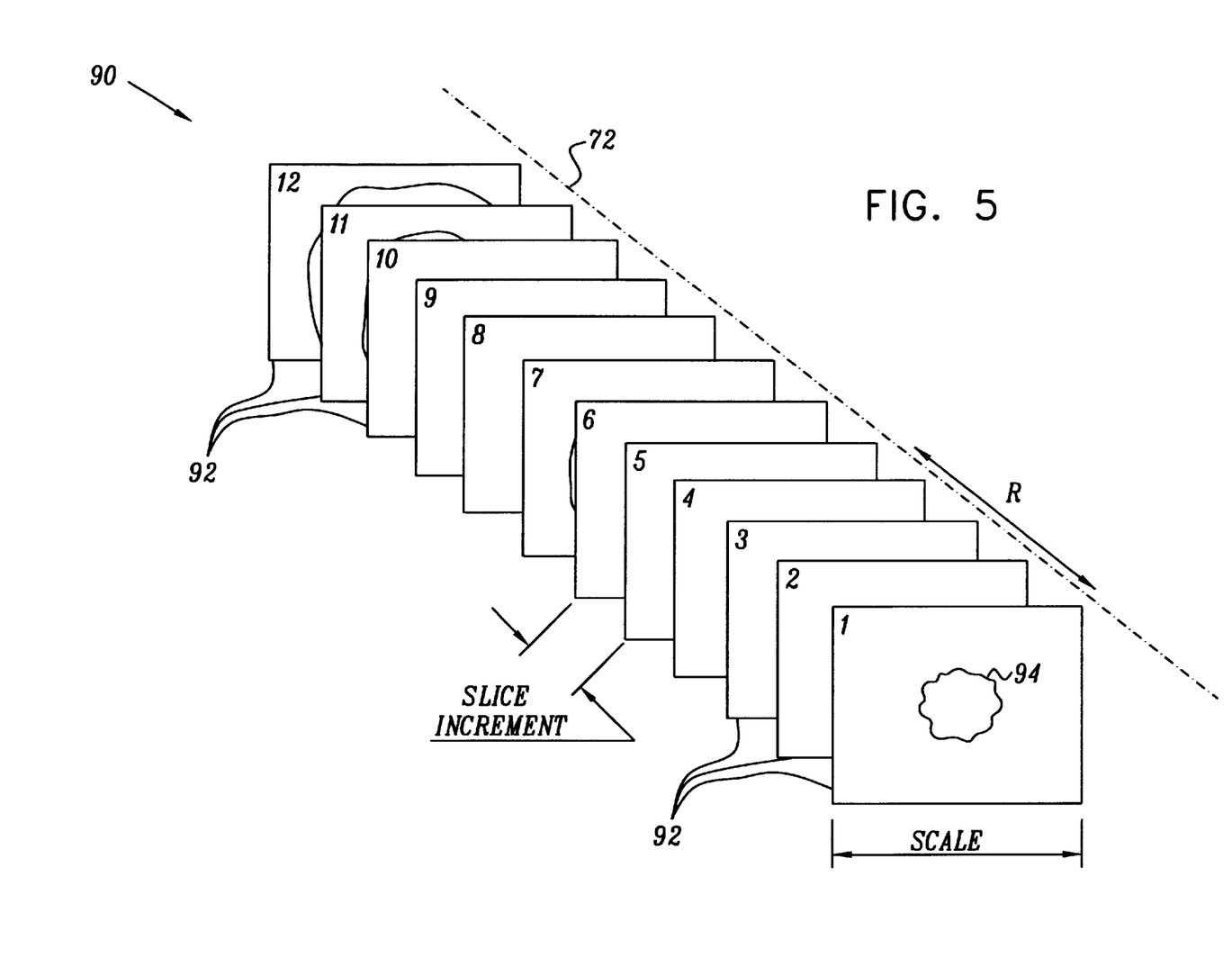
FIG. 5 is a schematic, exploded view of a 3D image of the heart, represented as a stack of parallel slices through the heart, in accordance with a preferred embodiment of the present invention.

FIG. 5 is a schematic, exploded view of a 3D diagnostic image 90 of heart 24, following registration of the 3D image with geometrical map 38, in accordance with a preferred embodiment of the present invention. This view is generated at a bullseye rendition step 56 in the method of FIG. 2. The bullseye rendition of image 90 comprises a stack of parallel slices 92, which are perpendicular to axis 72. The slices are preferably taken at a fixed slice increment one from another along the axis. Each slice shows a section 94 of image 90, at a distance R from apex 74 that is determined by the slice number.

Figure 6:
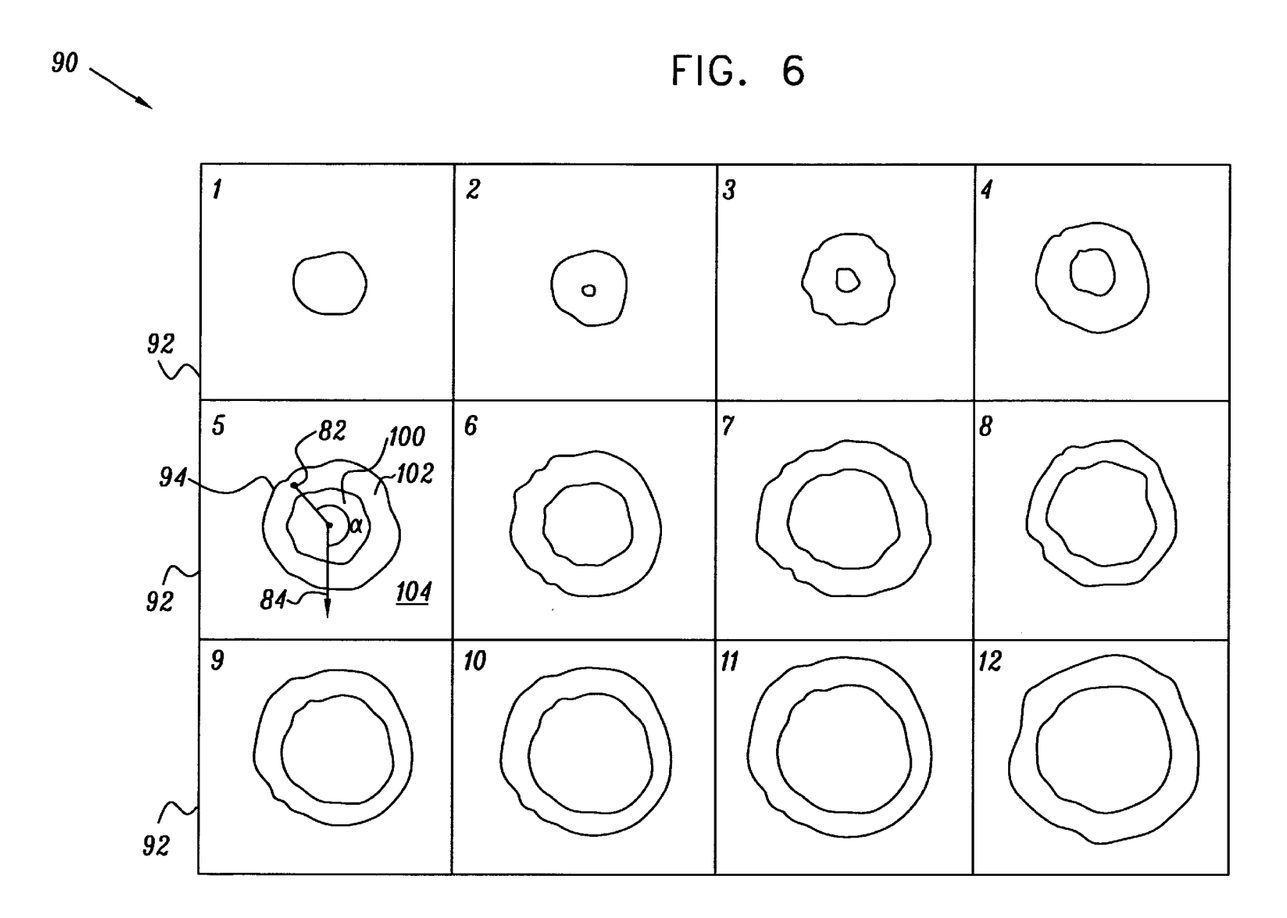
FIG. 6 shows the slices of FIG. 5 arrayed side-by-side, illustrating registration of the slices with the 3D map of FIG. 3, in accordance with a preferred embodiment of the present invention.

FIG. 6 shows slices 92 of image 90 arrayed side-by-side, illustrating extraction of diagnostic data from the slices for application to map 38, in accordance with a preferred embodiment of the present invention. Referring, for example, to slice number 5, sectional image 94 comprises three essential parts: an inner region 100, showing the inside of the ventricle; a wall region 102, showing the myocardium; and an outer region 104, external to the heart. The diagnostic information of interest is in region 102. Assuming image 90 to be a SPECT image, showing perfusion in the heart wall, for example, region 102 will typically have the highest value of perfusion.

At a coloration transfer step 58, the diagnostic information from each slice 92 is transferred to map 38. Each slice has a known value of distance R from apex 74. For each angle a within the slice, point 82 on surface 80 of the map (FIG. 4) is assumed to be the point at that angle that is located radially in the middle of region 102. In the case that image 90 is a perfusion image, point 82 is simply taken to be the point of highest perfusion at the given angle. In other imaging modalities, finding region 102 is, for the most part, similarly straightforward. The value of the diagnostic data at each point 82 is preferably represented as a color applied to the corresponding region of map 38.

Figure 7:
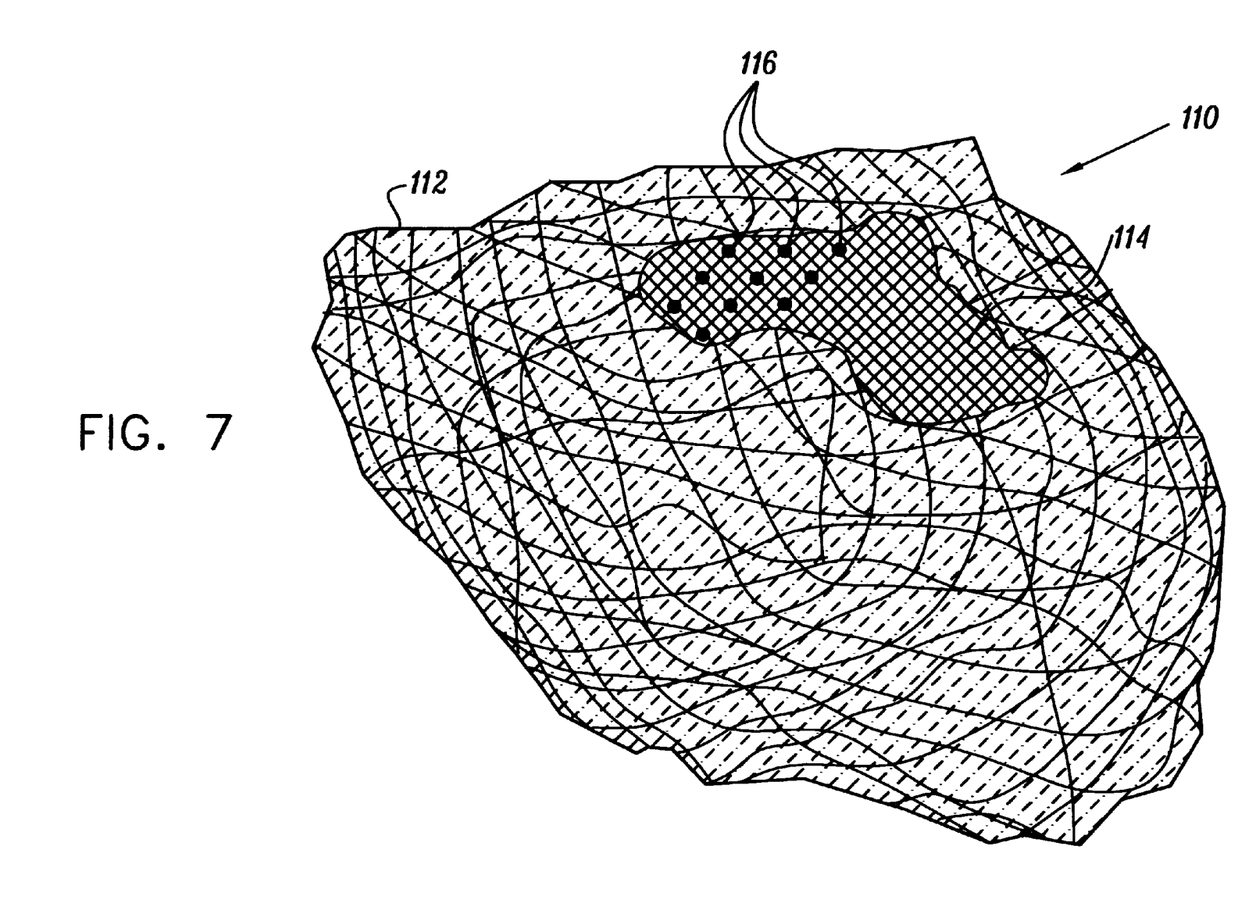
FIG. 7 is a schematic representation of the map of FIG. 3, after coloring of the map with diagnostic information from the image of FIGS. 5 and 6, in accordance with a preferred embodiment of the present invention.

FIG. 7 is a schematic representation of a colored geometrical map 110, as produced at step 58, in accordance with a preferred embodiment of the present invention. Because of the limited ability of a line drawing to convey qualities of a color image, only two different color regions appear on map 110: a well-perfused region 112, and an ischemic region 114. Preferably, the ischemic region has a darker or "cooler" color than the well-perfused region. In actual applications, in which display 36 comprises a color monitor, a broad range of different colors is used in map 110 to describe different levels of perfusion or of other diagnostic qualities.

Preferably, system 20 is operated by user 22 to carry out an invasive therapeutic procedure, guided by map 110, at a therapeutic step 60. In the present example, laser console 49 is operated to irradiate ischemic region 114 via catheter 30 with high-intensity laser radiation, as described in the above-mentioned PCT patent application PCT/IL97/00011. The laser creates revascularization channels in the myocardium, which are marked by system 20 with spots 116 on map 110. The combination of the imaging, mapping and therapeutic modalities enables the user to concentrate the treatment in the region of heart 24 that is known to need it, and to ensure that the region is fully covered. Other local therapeutic and diagnostic procedures can similarly benefit from the guidance provided by map 110.

Although preferred embodiments are described hereinabove with reference to heart 24, the principles of the present invention may similarly be applied to imaging, mapping and treatment of other organs and body structures. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

APPENDIX A

This appendix provides details of step 54 in the method of FIG. 2, in which two 3D representations, P and Q, of a chamber of heart 24 are brought into mutual registration. To begin, a rough estimate is found for the transformation between P and Q, either manually, or using the principle axis of a bounding ellipsoid or by principle component decomposition. The bounding ellipsoid technique is further described in the above-mentioned European patent application EP 0 974 936 and U.S. patent application Ser. No. 09/122,137.

Fine registration between P and Q is then preferably found using a variation of the Iterative Closest Point (ICP) algorithm. This algorithm is described by Besl and McKay in "A Method for Registration of 3D Shapes," published in *IEEE Transactions on Pattern Analysis and Machine Intelligence* 14(2):239–256 (1992), which is incorporated herein by reference. The following steps are repeated until convergence:

1. Nearest point search: For each point p in P find the closest point q on Q. One can take a subset of points of P to improve computation speed. Similarly, all points of Q can be covered, too, to ensure robustness.
2. Compute registration: Evaluate a transformation T that minimizes the sum of squared distances between pairs of closest points (p,q). The transformation is preferably either rigid, similarity, affine or projective as described below.
3. Transform: Apply the transformation T to all points in P.

Given two surfaces, P and Q, and two sets of points, $\{p_i \in P\}_{i=1}^n$, $\{q_i \in Q\}_{i=1}^n$, step 2 of this algorithm seeks a transformation, T, from a family of transformations (according to the possible families described below) that minimizes the mean square error, $\epsilon$, between the corresponding sets:

$$\varepsilon^2 = \frac{1}{n}\sum_{i=1}^{n} \|q_i - T(p_i)\|^2$$

Affine and Projective Transformations

For affine transformations, defined as T(p)=Ap+t, $$A = \begin{pmatrix} a_{11} & a_{12} & a_{13} \\ a_{21} & a_{21} & a_{23} \\ a_{31} & a_{32} & a_{33} \end{pmatrix}$$

is a 3×3 matrix, and $$t = \begin{pmatrix} t_1 \\ t_2 \\ t_3 \end{pmatrix}$$

is a translation vector.
We must minimize $$\varepsilon^2 = \frac{1}{n}\sum_{i=1}^{n} \|q_i - (Ap_i + t)\|^2.$$

Denoting $$p_i = \begin{pmatrix} x_{i1} \\ x_{i2} \\ x_{i3} \end{pmatrix}, \text{ and } q_i = \begin{pmatrix} y_{i1} \\ y_{i2} \\ y_{i3} \end{pmatrix},$$

and $q_i$=
we have three systems of equations:

$$\underbrace{\begin{pmatrix} x_{11} & x_{12} & x_{13} & 1 \\ x_{21} & x_{22} & x_{23} & 1 \\ \vdots & \vdots & \vdots & \vdots \\ x_{n1} & x_{n2} & x_{n3} & 1 \end{pmatrix}}_{X} \underbrace{\begin{pmatrix} a_{j1} \\ a_{j2} \\ a_{j3} \\ t_j \end{pmatrix}}_{a_j} = \underbrace{\begin{pmatrix} y_{1j} \\ y_{2j} \\ \vdots \\ y_{nj} \end{pmatrix}}_{y_j} \quad j = 1, 2, 3$$

Let a singular value decomposition of X be $X=UDV^T$. It then follows that $a_j = VDU^T y_j$.

Projective transformations are evaluated in a similar way to the affine case.

Similarity and Rigid Transformation

Whereas in affine transforms triangles are transformed to triangles, similarity transformations preserve proportions. We seek a scaling factor, c, a 3×3 rotation matrix, R, and a 3-dimensional translation vector, t, such that T(p)=cRp+t, wherein the error $$\varepsilon^2(R, T, c) = \frac{1}{n}\sum_{i=1}^{n} \|q_i - (cRp_i + t)\|^2$$

is minimized.

A suitable method for finding the desired similarity transform is described by Umeyama, in "Least-Squares Estimation of Transformation Parameters Between Two Point Patterns," published in *IEEE Transactions on Pattern Analysis and Machine Intelligence*, 13(4): 376–380 (1991), which is incorporated herein by reference. Define the center of mass of both P and Q:

$$\mu_p = \frac{1}{n}\sum_{i=1}^{n} p_i$$

$$\mu_q = \frac{1}{n}\sum_{i=1}^{n} q_i$$

Then define the variance of the points on both P and Q:

$$\sigma_p^2 = \frac{1}{n}\sum_{n=1}^{n} \|p_i - \mu_p\|^2$$

$$\sigma_q^2 = \frac{1}{n}\sum_{i=1}^{n} \|q_i - \mu_q\|^2$$

The covariance matrix between the two surfaces is $$\sum_{pq} = \frac{1}{n}\sum_{i=1}^{n} (q_i - \mu_q)(p_i - \mu_p)^T.$$

Let a singular value decomposition of $\Sigma_{pq}$ be $\Sigma_{pq}=UDV^T$, and $$S = \begin{cases} I & \text{if } det(U)\ det(V) = 1 \\ diag(1, 1, -1) & \text{if } det(U)\ det(V) = -1 \end{cases}$$

The rotation, translation and scaling of the transformation are then given by:

$$R = USV^T$$

$$t = \mu_q - cR\mu_p$$

$$c = \frac{1}{\sigma_p^2} trace(DS)$$

wherein the trace of a matrix is the sum of its diagonal elements.

In the case of rigid transformation no scaling is applied, so that c=1.

What is claimed is:

1. A method for mapping a structure in a body of a subject, comprising:
    capturing a three-dimensional (3D) image of the structure comprising diagnostic information;
    providing a probe having a position sensor for determining position and orientation information of the probe;
    generating a 3D geometrical map of the structure using a probe inserted into the structure and using the position sensor of the probe by contacting the probe with multiple points on the structure, each point having position and orientation information associated therewith and defined as a map point on the map;
    registering the image with the map, such that each of a plurality of image points in the image is identified with a corresponding map point in the map by performing a bullseye rendition of a stack of parallel slices of the image; and
    displaying the map, such that the diagnostic information associated with each of the image points is displayed at the corresponding map point.

2. A method according to claim 1, wherein the diagnostic information is related to blood flow in the structure.

3. A method according to claim 2, wherein the diagnostic information comprises local perfusion data.

4. A method according to claim 1, wherein the diagnostic information comprises metabolic data.

5. A method according to claim 1, wherein the diagnostic information is related to uptake of a substance in tissue of the structure.

6. A method according to claim 1, wherein the diagnostic information is related to motion of the structure.

7. A method according to claim 1, wherein generating the geometrical map comprises bringing the probe into contact with the structure at a multiplicity of locations on the structure, and recording position coordinates of the probe at the locations.

8. A method according to claim 7, wherein recording the position coordinates comprises determining the coordinates using the position sensor in the probe.

9. A method according to claim 1, wherein registering the image with the map comprises applying a transformation to at least one of the image and the map so that following the transformation, the image and the map have a common axis and a common scale.

10. A method according to claim 9, wherein registering the image with the map comprises dividing the image into a plurality of parallel planar slices, perpendicular to the axis and mutually spaced along the axis, and wherein the plurality of image points are located in the slices.

11. A method according to claim 10, wherein registering the image with the map comprises finding an axial coordinate of each of the slices and an angular coordinate of each of the image points located in each of the slices, and identifying each of the image points with the map point having the same axial and angular coordinates.

12. A method according to claim 11, wherein the structure comprises a wall defining a cavity, and wherein identifying each of the image points with the map point comprises finding, at the axial and the angular coordinate, the image point that is within a section of the wall.

13. A method according to claim 1, wherein displaying the map comprises coloring the map to reflect the diagnostic information.

14. A method according to claim 1, and comprising performing a medical procedure on the structure guided by the diagnostic information displayed on the map.

15. A method according to claim 14, wherein performing the medical procedure comprises using the probe to perform the procedure locally at locations selected on the geometrical map.

16. A method according to claim 15, and comprising marking on the geometrical map the locations at which the procedure was performed.

17. A method according to claim 15, wherein performing the medical procedure comprises performing a therapeutic procedure.

18. A method according to claim 17, wherein the diagnostic information relates to local blood flow in the structure, and wherein performing the therapeutic procedure comprises performing a procedure for improving the local blood flow.

19. A method according to claim 15, wherein performing the medical procedure comprises performing a diagnostic procedure.

20. A method according to claim 1, wherein the structure comprises a heart of the subject, and wherein generating the geometrical map comprises mapping an endocardial surface in a ventricle of the heart.

21. Apparatus for mapping a structure in a body of a subject, comprising:

an imaging device, adapted to capture a three-dimensional (3D) image of the structure comprising diagnostic information;

a probe having a position sensor for determining position and orientation information of the probe and adapted to be inserted into the structure, so as to generate a 3D geometrical map of the structure based on position and orientation information using the position sensor;

a processor, coupled to the probe and to the imaging device, and adapted to register the 3D image with the 3D geometrical map by performing a bullseye rendition of a stack of parallel slices of the 3D image, such that each of a plurality of image points in the 3D image is identified with a corresponding map point in the 3D geometrical map; and a display, coupled to be driven by the processor to display the 3D geometrical map, such that the diagnostic information associated with each of the image points is displayed at the corresponding map point.

22. Apparatus according to claim 21, wherein the diagnostic information is related to blood flow in the structure.

23. Apparatus according to claim 22, wherein the diagnostic information comprises local perfusion data.

24. Apparatus according to claim 21, wherein the diagnostic information comprises metabolic data.

25. Apparatus according to claim 21, wherein the diagnostic information is related to uptake of a substance in tissue of the structure.

26. Apparatus according to claim 21, wherein the diagnostic information is related to motion of the structure.

27. Apparatus according to claim 21, wherein to generate the geometrical map, the probe is brought into contact with the structure at a multiplicity of locations on the structure, and the processor records position coordinates of the probe at the locations.

28. Apparatus according to claim 27, wherein the position sensor is used for determining position information in the form of position coordinates.

29. Apparatus according to claim 21, wherein the processor is adapted to register the image with the map by applying a transformation to at least one of the image and the map so that following the transformation, the image and the map have a common axis and a common scale.

30. Apparatus according to claim 29, wherein the processor is further adapted to divide the image into a plurality of parallel planar slices, perpendicular to the axis and mutually spaced along the axis, wherein the plurality of image points are located in the slices.

31. Apparatus according to claim 30, wherein the processor is adapted to find an axial coordinate of each of the slices and an angular coordinate of each of the image points located in each of the slices, and to identify each of the image points with the map point having the same axial and angular coordinates.

32. Apparatus according to claim 31, wherein the structure comprises a wall defining a cavity, and wherein the processor is adapted to identify each of the image points with the map point by finding, at the axial and the angular coordinate, the image point that is within a section of the wall.

33. Apparatus according to claim 21, wherein the map is colored to reflect the diagnostic information.

34. Apparatus according to claim 21, and comprising a medical instrument adapted to perform a medical procedure on the structure guided by the diagnostic information displayed on the map.

35. Apparatus according to claim 34, wherein the medical instrument is contained in the probe, which is adapted to be used to perform the procedure locally at locations selected on the geometrical map.

36. Apparatus according to claim 35, wherein the processor is adapted to mark on the geometrical map the locations at which the procedure was performed.

37. Apparatus according to claim 35, wherein the medical procedure comprises a therapeutic procedure.

38. Apparatus according to claim 37, wherein the diagnostic information relates to local blood flow in the structure, and wherein the therapeutic procedure comprises a procedure for improving the local blood flow.

39. Apparatus according to claim 35, wherein the medical procedure comprises a diagnostic procedure.

40. Apparatus according to claim 21, wherein the geometrical map comprises a map of an endocardial surface in a ventricle of the heart.

* * * * *